(12) United States Patent
Dobbs

(10) Patent No.: US 10,195,612 B2
(45) Date of Patent: Feb. 5, 2019

(54) SMALL PARTICLE COMPOSITIONS AND ASSOCIATED METHODS

(71) Applicant: Primet Precision Materials, Inc., Ithaca, NY (US)

(72) Inventor: Robert J. Dobbs, Newfield, NY (US)

(73) Assignee: Primet Precision Materials, Inc., Ithaca, NY (US)

( * ) Notice: Subject to any disclaimer, the term of this patent is extended or adjusted under 35 U.S.C. 154(b) by 196 days.

(21) Appl. No.: 14/552,421

(22) Filed: Nov. 24, 2014

(65) Prior Publication Data

US 2015/0152303 A1    Jun. 4, 2015

Related U.S. Application Data

(63) Continuation of application No. 11/318,341, filed on Dec. 23, 2005, now abandoned.
(Continued)

(51) Int. Cl.
| | | |
|---|---|---|
| *B02C 17/00* | (2006.01) | |
| *B02C 17/20* | (2006.01) | |
| *A61K 9/14* | (2006.01) | |
| *B01J 21/06* | (2006.01) | |
| *B01J 23/644* | (2006.01) | |
| *B01J 37/00* | (2006.01) | |
| *B82Y 30/00* | (2011.01) | |
| *C01F 7/02* | (2006.01) | |
| *C01G 23/047* | (2006.01) | |
| *C09C 1/36* | (2006.01) | |

(Continued)

(52) U.S. Cl.
CPC ............... *B02C 17/20* (2013.01); *A61K 9/14* (2013.01); *B01J 21/063* (2013.01); *B01J 23/6447* (2013.01); *B01J 37/0036* (2013.01); *B82Y 30/00* (2013.01); *C01F 7/02* (2013.01); *C01F 7/023* (2013.01); *C01G 23/047* (2013.01); *C09C 1/36* (2013.01); *C09C 1/3623* (2013.01); *C09C 1/407* (2013.01); *C09K 3/1436* (2013.01); *H01M 4/9016* (2013.01); *H01M 4/921* (2013.01); *B01J 35/0013* (2013.01); *B01J 35/0046* (2013.01); *C01P 2004/04* (2013.01); *C01P 2004/20* (2013.01); *C01P 2004/30* (2013.01); *C01P 2004/54* (2013.01); *C01P 2004/62* (2013.01); *C01P 2004/64* (2013.01)

(58) Field of Classification Search
CPC ................................ B02C 17/20; B82Y 30/00
USPC .................... 241/184; 501/87; 977/773, 775
See application file for complete search history.

(56) References Cited

U.S. PATENT DOCUMENTS

| | | |
|---|---|---|
| 2,113,353 A | 4/1938 | McKenna |
| 2,581,414 A | 1/1952 | Hochberg |

(Continued)

FOREIGN PATENT DOCUMENTS

| | | |
|---|---|---|
| DE | 19758384 A1 | 7/1999 |
| FR | 2677012 A | 12/1992 |

(Continued)

OTHER PUBLICATIONS

Japanese Office Action dated Aug. 29, 2012 in connection with Application No. JP 2008-538050.
(Continued)

*Primary Examiner* — Faye Francis
(74) *Attorney, Agent, or Firm* — Wolf, Greenfield & Sacks, P.C.

(57) ABSTRACT

Milling methods that use grinding media particles formed of a ceramic material having an interlamellar spacing of less than 1250 nm.

6 Claims, 15 Drawing Sheets

Related U.S. Application Data

(60) Provisional application No. 60/731,307, filed on Oct. 27, 2005.

(51) Int. Cl.
  *C09C 1/40* (2006.01)
  *H01M 4/90* (2006.01)
  *H01M 4/92* (2006.01)
  *C09K 3/14* (2006.01)
  *B01J 35/00* (2006.01)

(56) References Cited

U.S. PATENT DOCUMENTS

| | | |
|---|---|---|
| 3,690,962 A | 9/1972 | Rudy |
| 3,737,289 A | 6/1973 | Rudy |
| 3,779,745 A | 12/1973 | Rudy |
| 3,840,367 A | 10/1974 | Rudy |
| 3,944,144 A | 3/1976 | Okada et al. |
| 4,066,451 A | 1/1978 | Rudy |
| 4,275,026 A | 6/1981 | Hazel et al. |
| 5,033,682 A | 7/1991 | Braun |
| 5,034,069 A | 7/1991 | Frarge et al. |
| 5,089,447 A | 2/1992 | Timm et al. |
| 5,215,945 A | 6/1993 | Dubensky et al. |
| 5,225,390 A | 6/1993 | Vogel et al. |
| 5,246,056 A | 9/1993 | Lomax et al. |
| 5,256,608 A | 10/1993 | Dubensky et al. |
| 5,261,477 A | 11/1993 | Brunet et al. |
| 5,310,605 A | 5/1994 | Baldoni et al. |
| 5,401,694 A | 3/1995 | Gesing et al. |
| 5,407,464 A | 4/1995 | Kaliski |
| 5,478,705 A | 12/1995 | Czekai et al. |
| 5,500,289 A | 3/1996 | Gavish |
| 5,518,187 A | 5/1996 | Bruno et al. |
| 5,663,512 A | 9/1997 | Schader et al. |
| 5,704,556 A | 1/1998 | McLaughlin |
| 5,756,409 A | 5/1998 | Van Dijen et al. |
| 5,918,103 A | 6/1999 | Kobayashi et al. |
| 5,993,506 A | 11/1999 | Kobayashi et al. |
| 6,017,504 A | 1/2000 | Kaliaguine et al. |
| 6,036,099 A | 3/2000 | Zhao et al. |
| 6,152,982 A | 11/2000 | Froes et al. |
| 6,231,636 B1 | 5/2001 | Froes et al. |
| 6,254,658 B1 | 7/2001 | Taniuchi et al. |
| 6,387,152 B1 | 5/2002 | Klassen et al. |
| 6,403,257 B1 | 6/2002 | Christian et al. |
| 6,520,837 B2 | 2/2003 | Weichert |
| 6,571,493 B2 | 6/2003 | Amano et al. |
| 6,604,698 B2 | 8/2003 | Verhoff et al. |
| 6,627,104 B1 | 9/2003 | Wang et al. |
| 6,634,576 B2 | 10/2003 | Verhoff et al. |
| 6,663,688 B2 | 12/2003 | Findeisen et al. |
| 6,669,747 B2 | 12/2003 | Salman |
| 7,140,567 B1 | 11/2006 | Dobbs |
| 2002/0047058 A1 | 4/2002 | Verhoff et al. |
| 2004/0126267 A1 | 7/2004 | DiSalvo et al. |
| 2004/0244675 A1 | 12/2004 | Kishimoto et al. |
| 2005/0155455 A1 | 7/2005 | Dobbs |
| 2005/0158227 A1 | 7/2005 | Dobbs |
| 2005/0158228 A1 | 7/2005 | Dobbs |
| 2005/0158229 A1 | 7/2005 | Dobbs |
| 2005/0158230 A1 | 7/2005 | Dobbs |
| 2005/0158231 A1 | 7/2005 | Dobbs et al. |
| 2005/0158232 A1 | 7/2005 | Dobbs |
| 2005/0158233 A1 | 7/2005 | Dobbs et al. |
| 2005/0158234 A1 | 7/2005 | Dobbs |
| 2005/0159494 A1 | 7/2005 | Dobbs |
| 2005/0161540 A1 | 7/2005 | Dobbs |
| 2005/0200035 A1 | 9/2005 | Dobbs |
| 2006/0003013 A1 | 1/2006 | Dobbs |
| 2006/0194057 A1 | 8/2006 | Pfluecker et al. |
| 2007/0098803 A1 | 5/2007 | Dobbs et al. |

FOREIGN PATENT DOCUMENTS

| | | |
|---|---|---|
| GB | 2164271 A | 3/1986 |
| JP | 4293557 A2 | 10/1992 |
| JP | 8276364 A2 | 10/1996 |
| JP | 10077491 | 3/1998 |
| JP | 2001-030175 A | 2/2001 |
| JP | 2001-527017 A | 12/2001 |
| JP | 2002-264023 A | 9/2002 |
| JP | 2003-206475 A | 7/2003 |
| JP | 2004-507343 A | 3/2004 |
| JP | 2005-289668 A | 10/2005 |
| JP | 2006-528550 A | 12/2006 |
| JP | 2006-528706 A | 12/2006 |
| WO | WO 2004/110699 A2 | 12/2004 |
| WO | WO 2007/016308 A2 | 2/2007 |
| WO | WO 2007/016528 A2 | 2/2007 |
| WO | WO 2007/086967 A2 | 8/2007 |

OTHER PUBLICATIONS

International Search Report dated May 7, 2008 in connection with Application No. PCT/US2006/042182.

International Search Report dated May 12, 2006 in connection with Application No. PCT/US2005/007743.

International Search Report and Written Opinion dated Jan. 31, 2006 in connection with Application No. PCT/US2005/007744.

Artyukh et al., Physicochemical reactions of tungsten carbides with hafnium carbide. Izv. Akad. Nauk SSSR, Neorg Mater. 1976;4:634-637.

Eremenko et al., Investigations of alloys or the ternary systems W—HfC—C and W—ZrC—C at subsolidus temperatures. Dokl. Akad. Nauk. Ukr. SSSR, Ser. A No. 1. 1976:80-88.

Velikanova et al., Effect of alloying on the structure and properties of cast WC1-x Materials. Poroshkovaya Metallurgiya. 1981;2(218):53-58.

SMALL PARTICLE COMPOSITIONS AND ASSOCIATED METHODS

RELATED APPLICATIONS

This application is a continuation of U.S. application Ser. No. 11/318,341, filed Dec. 23, 2005, which claims priority to U.S. Provisional Patent Application Ser. No. 60/731,307, filed Oct. 27, 2005, which are incorporated herein by reference in their entirety.

FIELD OF INVENTION

The invention relates generally to small particle compositions, as well as methods (e.g., milling methods) and components associated with such particle compositions.

BACKGROUND OF INVENTION

Particle reduction (also known as comminution) is a very old technology, practiced, for example, by the ancients to produce flour from grain by stone wheel grinding. More refined techniques, such as milling, were developed to produce smaller and more regular powders for use in a variety of industrial applications. Milling processes typically use grinding media to crush, or beat, a product material to smaller dimensions. For example, the product material may be provided in the form of a powder having relatively large particles and the milling process may be used to reduce the size of the particles. Mills typically operate by distributing product material around grinding media and rotating to cause collisions between grinding media that fracture product material particles into smaller dimensions.

Particle compositions having extremely small particle sizes (e.g., nanometer-sized and lower) are proving to be useful for many new applications. However, certain conventional milling methods may be limited in their ability to produce such compositions at very small particle sizes and/or with other features related to particle morphology, topology and/or crystallography. Other processes for producing small particles, such as chemical precipitation and sol-gel, have also been utilized. However, precipitation processes may also have some of the above-noted limitations. In addition, precipitation processes may use relatively long processing times and result in high costs.

SUMMARY OF INVENTION

Small particle compositions, as well as methods and components associated with the same, are described.

In one aspect, a nanoparticle composition is provided. The nanoparticle composition comprises nanoparticles having a lenticular cross-section including a thickness that decreases from a center portion to edge portions of the nanoparticles. The nanoparticles have an average particle size of less than 150 nm.

In another aspect, a nanoparticle composition is provided. The nanoparticle composition comprises nanoparticles having an average particle size of less than 150 nm, wherein the nanoparticles have a stepped surface.

In another aspect, a nanoparticle composition is provided. The nanoparticle composition comprises nanoparticles having an average particle size of less than 150 nm and a crystallographic orientation. A majority of the nanoparticles have the same crystallographic orientation.

In another aspect, a nanoparticle composition is provided. The nanoparticle composition comprises nanoparticles having an average particle size of less than 150 nm and a crystallographic orientation. The nanoparticles are substantially free of carbon-based surface residue.

In another aspect, a method of producing nanoparticles is provided. The method comprises milling feed particles to form a milled nanoparticle composition including nanoparticles having a lenticular cross-section including a thickness that decreases from a center portion to edge portions of the nanoparticles. The nanoparticles have an average particle size of less than 150 nm.

In another aspect, a method of producing nanoparticles is provided. The method comprises milling feed particles to form a milled nanoparticle composition including nanoparticles having an average particle size of less than 150 nm. The nanoparticles have a stepped surface.

In another aspect, a method of producing nanoparticles is provided. The method comprises milling feed particles to form a milled nanoparticle composition including nanoparticles having an average particle size of less than 150 nm and a crystallographic orientation. A majority of the nanoparticles have the same crystallographic orientation.

In another aspect, a method is provided. The method comprises milling feed nanoparticles having an average particle size of less than 150 nm to produce surface features on the nanoparticles. The method further comprises recovering the nanoparticles including surface features having an average particle size within about 25% of the average particle size of the feed particles.

In another aspect, a method is provided. The method comprises milling particles having a first composition and particles having a second composition in a milling apparatus. The method further comprises forming a region comprising the second composition on respective surfaces of particles having the first composition.

In an aspect of the invention, grinding media are provided. The grinding media comprise grinding media particles formed of a material having a density of greater than 8 grams/cubic centimeter, a hardness of greater than 900 kgf/mm2, and a fracture toughness of greater than 6 MPa/m1/2.

In another aspect of the invention, grinding media are provided. The grinding media comprise grinding media particles formed of a ceramic material. The ceramic material have an interlamellar spacing of less than 1250 nm.

In another aspect of the invention, grinding media are provided. The grinding media comprise grinding media particles having an average particle size of less than about 150 micron, wherein the particles are formed of a material having a toughness of greater than 6 MPa/m1/2.

In another aspect of the invention, grinding media are provided. The grinding media comprise grinding media particles comprising a core material and a coating formed on the core material. The coating includes a plurality of layers, at least one of the layers having a thickness of less than 100 nanometers.

In another aspect of the invention, grinding media are provided. The grinding media comprise grinding media particles formed of a nanocrystalline composite comprising a plurality of nanoparticles dispersed in a matrix material.

In another aspect of the invention, grinding media are provided. The grinding media comprise grinding media particles formed of a composite comprising a plurality of particles dispersed in a matrix material, wherein the dispersed particles are formed of a material having a density of greater than 8 grams/cubic centimeter.

In another aspect of the invention, grinding media are provided. The grinding media comprise grinding media particles formed of a ceramic compound comprising more than one metal element, the particles having an average size of less than about 150 micron.

In another aspect of the invention, grinding media are provided. The grinding media comprise grinding media particles capable of milling inorganic feed particles to produce an inorganic milled particle composition having an average particle size of less than 100 nm and a contamination level of less than 500 ppm. The feed particles have an average particle size of greater than 10 times the average particle size of the milled particle composition.

In another aspect of the invention, grinding media are provided. The grinding media comprise grinding media particles capable of milling titania feed particles to produce a titania milled particle composition at a specific energy input of less than about 25,000 kJ/kg. The titania milled particle composition has an average particle size of less than about 100 nm and a contamination level of less than 500 ppm. The titania feed particles have an average particle size of greater than 50 times the average particle size of the milled titania particle composition.

In another aspect of the invention, grinding media are provided. The grinding media comprise grinding media particles such that at least 70% of the grinding media particles have an average particle size of less than about 150 micron and are capable of passing a steel plate compression test.

In another aspect of the invention, a milled particle composition is provided. The composition comprises milled inorganic particles having an average particle size of less than 100 nm and a contamination level of less than 500 nm.

In another aspect of the invention, a method is provided. The method comprises milling inorganic feed particles using grinding media to produce an inorganic milled particle composition having an average particle size of less than 100 nm and a contamination level of less than 500 ppm. The feed particles have an average particle size of greater than 10 times the average particle size of the milled particle composition.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure. Nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Figure 1:
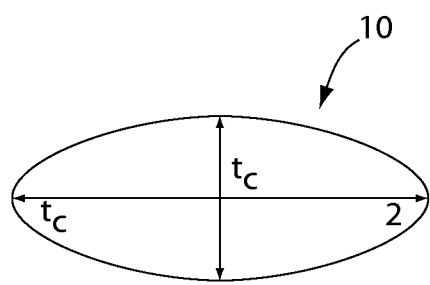
FIG. 1 shows a representative cross-section of a lenticular particle according to an embodiment of the invention.

The invention provides small particle compositions. The particle compositions, in some cases, are characterized by having an extremely small average particle size (e.g., 1 micron or less). As described further below, the particle compositions may be produced in a milling process that uses preferred types of grinding media and/or preferred milling conditions. The process may be controlled to produce small particle compositions having one or more desired features related to particle morphology (e.g., lenticular-shaped), topology (e.g., stepped surfaces) and crystallographic orientation. The small particle size coupled with such feature(s) can lead to significant property advantages in a variety of different applications including catalytic applications.

The particle compositions may be produced at very small particle sizes. In some embodiments, the average particle size of the composition is less than 1 micron. In certain embodiments, the average particle size may be even smaller. For example, the average particle size may be less than 600 nm, less than 250 nm, or less than 100 nm. In some cases, it is even possible to produce particle compositions having an average particle size of less than 50 nm, or less than 10 nm. Such particle sizes may be obtained, in part, by using grinding media having certain preferred characteristics, as described further below.

The preferred average particle size of the composition typically depends on the intended application. In certain applications, it may be desired for the average particle size to be extremely small (e.g., less than 100 nm); while, in other applications, it may be desired for the average particle size to be slightly larger (e.g., between 100 nm and 1 micron). In general, milling parameters may be controlled to provide a desired particle size, though in certain cases it may be preferable for the average particle size to be greater than 1 nm to facilitate milling. For example, the average particle size of the milled material may be controlled by a number of factors including grinding media characteristics (e.g., density, size, hardness, toughness), as well as milling conditions (e.g., specific energy input).

It should be understood that the average particle size of a particle composition may be determined by measuring an average cross-sectional dimension (e.g., diameter for substantially spherical particles) of a representative number of particles. For example, the average cross-sectional dimension of a substantially spherical particle is its diameter; and, the average cross-sectional dimension of a non-spherical particle is the average of its three cross-sectional dimensions (e.g., length, width, thickness), as described further below. The particle size may be measured using a laser particle measurement instrument, a scanning electron microscope or other conventional techniques.

It should also be understood that particle compositions having average particle sizes outside the above-described ranges (e.g., greater than 1 micron) may be useful in certain embodiments of the invention.

The particle compositions may also be relatively free of large particles. That is, the particle compositions may include only a small concentration of larger particles. For example, the $D_{90}$ values for the compositions may be any of the above-described average particle sizes. Though, it should be understood that the invention is not limited to such $D_{90}$ values.

The particle compositions may also have a very high average surface area. The high surface area is, in part, due to the very small particle sizes noted above. The average surface area of the particle compositions may be greater than 1 $m^2/g$; in other cases, greater than 5 $m^2/g$; and, in other cases, greater than 50 $m^2/g$. In some cases, the particles may have extremely high average surface areas of greater than 100 $m^2/g$; or, even greater than 500 $m^2/g$. It should be understood that these high average surface areas are even achievable in particles that are substantially non-porous, though other particles may have surface pores. Such high surface areas may be obtained, in part, by using grinding media having certain preferred characteristics, as described further below.

Similar to particle size, the preferred average surface area of the particle composition typically depends on the intended application. In certain applications, it may be desired for the average surface area to be extremely large (e.g., greater than 50 $m^2/g$); while, in other applications, it may be desired for the average surface area to be slightly smaller (e.g., between 50 $m^2/g$ and 1 $m^2/g$). In general, milling parameters may be controlled to provide a desired surface area, though in certain cases it may be preferable for the average surface area to be less than 3,000 $m^2/g$ (e.g., for substantially non-porous particles). For example, the average surface area of the milled particle compositions may be controlled by a number of factors including grinding media characteristics (e.g., density, size, hardness, toughness), as well as milling conditions (e.g., energy, time).

As described further below, the particles of the present invention can be produced in a milling process. Thus, these particle compositions may be described as having a characteristic "milled" morphology/topology. Those of ordinary skill in the art can identify "milled particles" as particles that include one or more of the following microscopic features: multiple sharp edges, faceted surfaces, and being free of smooth rounded "corners" such as those typically observed in chemically-precipitated particles. It should be understood that the milled particles described herein may have one or more of the above-described microscopic features, while having other shapes (e.g., lenticular, spherical) when viewed at lower magnifications.

In some embodiments, the particles have a lenticular morphology. The lenticular particles may have a shape defined around an elliptical plane and bounded by curved (e.g., lens-shaped) surfaces. FIG. 1 shows a representative cross-section of a lenticular particle 10. As shown, a thickness of the center portion ($t_c$) of the particle is greater than a thickness of the edge portion ($t_e$) of the particle. In some embodiments, ($t_c$) is about 5 times greater than ($t_e$) (e.g., between about 5 and 10 times greater); and, in some embodiments, ($t_c$) is about 10 times greater than ($t_e$).

Lenticular particles also may be characterized by a dimension (d) perpendicular to the respective thicknesses. In embodiments in which lenticular particles have a substantially circular cross-section defining a plane perpendicular to the lens-shaped cross-section, dimension (d) is the diameter of the circular cross-section. However, it should be understood that the cross-section of a lenticular particle perpendicular to the lens-shaped cross-section may not be spherical and, thus, dimension (d) does not refer to a diameter. For example, the cross-section of a lenticular particle perpendicular to the lens-shaped cross-section may be elliptical.

In certain embodiments, (d) is greater than or equal to about 10 times ($t_c$); and, in some embodiments, (d) is greater than or equal to about 7 times ($t_c$).

It should be understood that the average particle size of a composition including lenticular particles may be determined by measuring the average cross-sectional dimension of a representative number of particles. The average cross-sectional dimension is the average of the three cross-sectional dimensions of the particle. For a lenticular particle having a circular cross-section perpendicular to its lens-shaped cross-section the average cross-sectional dimension is $(2\times(d)+(t_c))/3$.

Lenticular particles may be particularly desired when the compositions are used in catalytic applications. Without being bound by any theory, it is believed that such a shape can increase the number of catalytic sites on particle surfaces, as described further below.

In other embodiments, the particles may not be lenticular. For example, the particles may have a substantially spherical, or oblate spheroid shape, amongst others. The particles may be platelets. It should be understood that a particle composition may include particles having one or more of the above-described shapes.

In some embodiments, the particles have a stepped-surface topography. That is, the particle surface defines a series of steps. In some cases, it may be preferable for the particles to include a high density of steps; that is, a high number of steps per unit area. In some cases, the length-to-height ratio of the steps may be small. In some embodiments, the particles include one or more steps having a height of greater than about 5 nm (e.g., between about 5 nm and about 20 nm); in some embodiments, the step height is less than about 10 nm, or less than about 5 nm. In some cases, where the step height is less than about 5 nm, it should be understood that the step height may be below the resolution of instrument (e.g., AFM) used to examine the step height. In such cases, other considerations, may be used to determine the presence of such step heights. In some embodiments, the particles include one or more steps having a width of greater than about 5 nm (e.g., between about 5 nm and about 20 nm); in some embodiments, the step width is less than about 10 nm or less than about 5 nm.

The step density on milled particles of the invention may be significantly higher than that of similarly shaped particles produced using conventional chemical precipitation techniques. Without being bound by any theory, it is believed the steps on milled particles of the invention are produced as a result of mechanical forces (e.g., particle-grinding media contact). In contrast, the production of steps on chemically-precipitated particles is dictated by free-energy considerations. It is believed that it is possible to produce many more steps by properly selecting milling conditions than those that generally arise from free-energy considerations during chemical precipitation.

The surface topography of a particle may be characterized by atomic force microscopy (AFM). For example, AFM may be used to generate a surface map that can be used to observe the steps. Also, high-resolution TEM may be used to examine surface topography.

A lenticular particle shape is particularly conducive to having stepped surfaces. However, it should be understood that particles having other morphologies may also have stepped surfaces.

Particles having a high density of surface steps may be particularly desired when the compositions are used in catalytic applications. Without being bound by any theory, it is believed that each step may function as a catalytic site and, thus, increasing the number of steps on a particle surface can increase the number of catalytic sites and surface area.

In some embodiments, the compositions of the invention may comprise particles having a preferred crystallographic orientation. In these embodiments, a majority (i.e., greater than 50%) of the particles in a composition may have the same crystallographic orientation. In other embodiments, greater than 75% of the particles, or even greater than 95%, or even substantially all, of the particles in a composition may have the same crystallographic orientation.

The preferred crystallographic orientation of the particles may depend, in part, on the crystal structure (e.g., hexagonal, tetragonal) of the material that forms the particles. Crystals generally preferentially fracture along specific planes with characteristic amounts of energy being required to induce fracture along such planes. During milling, such energy results from particle/grinding media collisions. It is observed that, by controlling the energy of such collisions via milling parameters (e.g., specific energy input), it is possible to preferentially fracture particles along certain crystallographic planes which creates a particle composition having a preferred crystallographic orientation.

In some embodiments, the preferred crystallographic orientation is defined by a basal plane (i.e., the plane which is perpendicular to the principal axis (c axis) in a tetragonal or hexagonal structure). For example, the basal plane, and crystallographic orientation, may be the (0001) or (001) plane.

Crystallographic orientation of particles may be measured using known techniques. A suitable technique is x-ray diffraction (XRD). It may be possible to assess the relative percentage of particles having the same preferred crystallographic orientation using XRD.

Particle compositions having a preferred crystallographic orientation may be particularly desired when the compositions are used in catalytic applications. Because certain planes can exhibit enhanced catalytically activity for certain reactions, it may be possible to significantly increase the overall catalytic activity of a particle composition by exposing such planes. As noted above, it is believed that milling conditions may be controlled to preferentially fracture particles along certain crystallographic planes which may be especially catalytically active for certain reactions, thus, creating a particle composition that has a dramatically high catalytic activity for such reactions.

In some embodiments, the material composition along the exposed crystallographic orientation may also affect catalytic activity. For example, the material composition of the exposed plane in an ordered intermetallic compound particle composition (which are described further below) may be important in determining catalytic activity. It may be desired to expose planes that have high catalytic activity. For example, for a Pt—Bi ordered intermetallic compound particle composition, the preferred crystallographic orientation may be the (001) Pt plane (i.e., the Pt—Pt plane) which is highly catalytic for a number of reactions (e.g., fuel oxidation).

In some embodiments, particles may be substantially free (and/or, entirely free) of surface contamination that may result from certain chemical precipitation processes because particles of the invention may be produced by milling. The surface contamination (often in the form of a layer or a portion of a layer) that results from certain chemical precipitation typically processes comprises element(s) from precursors used to form the particles. These precursors may comprise organic compounds (and, thus, also comprise carbon). Thus, in some embodiments, particles of the invention may be substantially free (and/or, entirely free) of surface contamination comprising organic compounds such as carbon-based surface contamination. In this context, "substantially free of organic compounds" refers to carbon concentration levels of less than 200 ppm. "Surface contamination", in this context, refers to any species (e.g., compound, element, etc.) that is present on the particle surface and has a different composition than the composition of the particle. Such low surface contamination concentrations are even achievable when the particles are metallic (e.g., pure metals, alloys, intermetallic compounds).

In some embodiments, the particles may be substantially-free of halogen (e.g., chlorine)-based surface contamination (i.e., halogen concentration levels of less than 200 ppm). Precursors used in chemical processes also may comprise halogens (e.g., chlorine).

Surface contamination concentrations may be determined by known techniques. For example, thermal gravimetric analysis (TGA), Raman Spectroscopy, or GDMS mass spectroscopy may be suitable to determine such concentrations.

It should be understood that in these embodiments in which particles are substantially free of the above-described types of surface contamination, other types of surface contamination may be present. For example, oxide-based surface contamination may be formed on a portion, or the entire, particle surface as a result of oxidation processes (e.g., when particles are exposed to air). However, in other embodiments, the particles may be substantially free of all types of surface contamination. Even particles of the invention that would otherwise oxidize if exposed to air may be substantially free of all types of surface contamination by dispersing such particles in a suitable liquid (e.g., water-based, organic-based).

Minimization of surface contamination (e.g., carbon-based surface contamination) is preferable in certain applications in which particle compositions of the invention are used. For example, in catalytic applications, it may be preferable to minimize surface contamination which would otherwise inhibit catalytic activity. Thus, particles being relatively free of the above-noted types of surface contamination may have enhanced catalytic activity.

An advantage of certain embodiments of the invention is that the above-noted particle sizes can be achieved at very low contamination levels. The grinding media properties and/or compositions noted above may enable the low contamination levels because such characteristics lead to very low wear rates. For example, the contamination levels may be less than 900 ppm, less than 500 ppm, less than 200 ppm, or even less than 100 ppm. In some processes, virtually no contamination may be detected which is generally representative of contamination levels of less than 10 ppm. As used herein, a "contaminant" is grinding media material introduced into the product material composition during milling. It should be understood that typical commercially available product materials may include a certain impurity concentration (prior to milling) and that such impurities are not includes in the definition of contaminant as used herein. Also, other sources of impurities introduced in to the product material, such as material from the milling equipment, are not included in the definition of contaminant as used herein. The "contamination level" refers to the weight concentration of the contaminant relative to the weight concentration of the milled material. Typical units for the contamination level are ppm. Standard techniques for measuring contamination levels are known to those of skill in the art including chemical composition analysis techniques.

It should be understood that methods of the invention may produce compositions having any of the above-described particle size values (including values of relative size between particles before and after milling) combined with any of the above-described contamination levels. For example, one method of the invention involves milling feed particles having an average initial particle size to form a milled particle composition having an average final particle size of less than 100 nm, wherein the initial particle size is greater than 100 times the final particle size and the milled particle composition has a contamination level of less than 500 ppm.

As noted above, particle compositions of the invention may have enhanced catalytic activity. Catalytic activity may be characterized by chemisorption techniques as described further below in the Example 1.

Particle compositions having enhanced catalytic activity are suitable for use as catalysts in a number of applications including fuel cells. When used in fuel cells, such particle compositions may be incorporated into one or more of the electrodes (e.g., anodes, cathodes). The particle compositions catalyze reactions that occur at the electrode(s) (e.g., oxidation of fuel) and, thus, enhance fuel cell performance (e.g., onset potential and peak current). Catalytic performance of the particle compositions are further described in the examples below.

The particle compositions may be of a variety of material compositions. Suitable material compositions include metals (such as cobalt, molybdenum, titanium, tungsten), metal compounds (such as intermetallic compounds, metal hydrides or metal nitrides), metal alloys, ceramics (including oxides, such as titanium oxide (titania), aluminum oxide ($Al_2O_3$), and carbides such as silicon carbide) and diamond, amongst many others. As described further below, in some embodiments, the particles are formed of a catalytic material. In some cases, the catalytic material may be consumed, in part, when catalyzing the desired reactions; in other cases, the catalytic material catalyzes the reaction without being consumed.

In some embodiments, it may be preferred for the material composition to be formed of a crystalline material or semi-crystalline material. In some cases, it is preferred that the crystalline material have an anisotropic crystal structure (e.g., hexagonal, tetragonal, rhombohedral and the like). It may be easier to produce particles having one or more of the above-described characteristics (e.g., lenticular morphology, stepped-surface topography, preferred crystallographic orientation) using such material compositions. Without being bound by any theory, it is believed that such structures may fracture in ways that lead to such characteristics. For example, aluminum oxide ($Al_2O_3$) particles have a rhombohedral structure and may be used to produce particle compositions having a lenticular morphology, stepped-surface topography and preferred crystallographic orientation.

In some embodiments, it may be preferred for the particle composition to be formed of a material that is relatively brittle. In general, brittle materials fracture with lower energies and less deformation than ductile materials. Such fracture behavior may facilitate production of particles having one or more of the above-described features. Those of ordinary skill in the art can determine whether a material is brittle using standard measurement techniques such as a Charpy Impact test.

In certain embodiments, particularly when used in catalytic applications, it may be preferred that the particles are formed of an ordered intermetallic compound composition. As used herein, the term "ordered intermetallic compound" refers to compounds that comprise more than one metal and have an ordered atomic structure. In an ordered intermetallic compound, substantially all unit cells include the same arrangement of metal atoms. Suitable ordered intermetallic compounds are described in U.S. Patent Application Publication No. 20040126267, based on U.S. patent application Ser. No. 10/630,237, entitled "Intermetallic Compounds for use as Catalysts and Catalytic Systems", filed Jul. 29, 2003, which is incorporated herein by reference. Ordered intermetallic compounds are to be distinguished from metal alloys and metal solid solutions. Metal alloys and metal solid solutions do not have an ordered atomic structure, as described above.

Examples of suitable intermetallic compounds that may be used in accordance with the invention include, but are not limited to, PtBi, $PtBi_2$, PtIn, PtPb, PtGe, $PtIn_2$, $PtIn_3$, $Pt_3In_7$, PdGe, PdSb, IrBi, NiBi, PtSn, $PtSn_2$, $Pt_3Sn$, $Pt_2Sn_3$, $PtSn_4$, PtSb, $PtSb_2$, RhBi, PtGa, $PtCd_2$, PtMn and BiPd. PtBi may be particularly preferred in certain applications. Other ordered intermetallic compounds also may be used in accordance with the invention including other intermetallic compounds that comprise the aforementioned elements at different stoichiometries.

One aspect of the invention is the discovery that particle compositions having the features described above can be produced in a milling process. The features are achievable by using grinding media having selected characteristics (e.g., density, mechanical properties, size) and controlling milling conditions, as described further below.

In some embodiments, the grinding media is formed of a material having a density of greater than 6 grams/cm$^3$; in some embodiments, greater than 8 grams/cm$^3$; in some embodiments, the density is greater than 10 grams/cm$^3$; or greater than 15 grams/cm$^3$; or, even, greater than 18 grams/cm$^3$. Though, in certain embodiments, the density of the grinding media may be less than 22 grams/cm$^3$, in part, due to difficulties in producing suitable grinding materials having greater densities. It should be understood that conventional techniques may be used to measure grinding media material density.

In certain embodiments, it also may be preferable for the grinding media to be formed of a material having a high fracture toughness. For example, in some cases, the grinding media is formed of a material having a fracture toughness of greater than 6 MPa/m$^{1/2}$; and in some cases, the fracture toughness is greater than 9 MPa/m$^{1/2}$. The fracture toughness may be greater than 12 MPa/m$^{1/2}$ in certain embodiments.

Conventional techniques may be used to measure fracture toughness. Suitable techniques may depend, in part, on the type of material being tested and are known to those of ordinary skill in the art. For example, an indentation fracture toughness test may be used. Also, a Palmqvist fracture toughness technique may be suitable, for example, when testing hard metals.

It should be understood that the fracture toughness values disclosed herein refer to fracture toughness values measured on bulk samples of the material. In some cases, for example, when the grinding media are in the form of very small particles (e.g., less than 150 micron), it may be difficult to measure fracture toughness and the actual fracture toughness may be different than that measured on the bulk samples.

In certain embodiments, it also may be preferable for the grinding media to be formed of a material having a high hardness. It has been found that media having a high hardness can lead to increased energy transfer per collision with product material which, in turn, can increase milling efficiency. In some embodiments, the grinding media is formed a material having a hardness of greater than 75 kgf/mm$^2$; and, in some cases, the hardness is greater than 200 kgf/mm$^2$. The hardness may even be greater than 900 kgf/mm$^2$ in certain embodiments. Conventional techniques may be used to measure hardness. Suitable techniques depend, in part, on the type of material being tested and are known to those of ordinary skill in the art. For example, suitable techniques may include Rockwell hardness tests or Vickers hardness tests (following ASTM 1327). It should be understood that the hardness values disclosed herein refer to hardness values measured on bulk samples of the material. In some cases, for example, when the grinding media are in the form of very small particles (e.g., less than 150 micron), it may be difficult to measure hardness and the actual hardness may be greater than that measured on the bulk samples.

It should be understood that not all milling processes of the present invention use grinding media having each of the above-described characteristics.

The grinding media may have a wide range of dimensions. In general, the average size of the grinding media is between about 0.5 micron and 10 cm. The preferred size of the grinding media used depends of a number of factors including the size of the feed particles, desired size of the milled particle composition, grinding media composition, and grinding media density, amongst others.

In certain embodiments, it may be advantageous to use grinding media that are very small. It may be preferred to use grinding media having an average size of less than about 250 microns; or, less than about 150 microns (e.g., between about 75 and 125 microns). In some cases, the grinding media may have an average size of less than about 100 microns; or even less than about 10 microns. Grinding media having a small size have been shown to be particularly effective in producing particle compositions having very small particle sizes (e.g., less than 1 micron). In some cases, the grinding media may have an average size of greater than 0.5 micron.

It should be understood that the average size of grinding media used in a process may be determined by measuring the average cross-sectional dimension (e.g., diameter for substantially spherical grinding media) of a representative number of grinding media particles. The grinding media size may be measured using conventional techniques such as suitable microscopy techniques or standard sieve size screening techniques.

The grinding media may also have a variety of shapes. In general, the grinding media may have any suitable shape known in the art. In some embodiments, it is preferred that the grinding media be substantially spherical (which may be used herein interchangeably with "spherical"). Substantially spherical grinding media have been found to be particularly effective in obtaining desired milling performance.

It should also be understood that any of the grinding media used in methods of the invention may have any of the characteristics (e.g., properties, size, shape, composition) described herein in combination with one another. For example, grinding media used in methods of the invention may have any of the above-noted densities and above-noted average sizes (e.g., grinding media may have a density of greater than about 6 grams/cm$^3$ and an average size of less than about 250 micron).

The above-described grinding media characteristics (e.g., density, hardness, toughness) are dictated, in part, by the composition of the grinding media. In certain embodiments, the grinding media may be formed of a metallic material including metal alloys or metal compounds. In one set of embodiments, it may be preferred that the grinding media are formed of ferro-tungsten material (i.e., Fe—W). In some cases, the compositions may comprise between 75 and 80 weight percent iron and between 20 and 25 weight percent tungsten. In some cases, ferro-tungsten grinding media may be carburized to improve wear resistance.

In other embodiments, the grinding media may be formed of a ceramic material such as a carbide material. In some embodiments, the grinding media to be formed of a single carbide material (e.g., iron carbide ($Fe_3C$), chromium carbide ($Cr_7C_3$), molybdenum carbide ($Mo_2C$), tungsten carbide (WC, $W_2C$), niobium carbide (NbC), vanadium carbide (VC), and titanium carbide (TiC)). In some cases, it may be preferred for the grinding media to be formed of a multi-carbide material. A multi-carbide material comprises at least two carbide forming elements (e.g., metal elements) and carbon.

A multi-carbide material may comprise a multi-carbide compound (i.e., a carbide compound having a specific stoichiometry; or, a blend of single carbide compounds (e.g., blend of WC and TiC); or, both a multi-carbide compound and a blend of single carbide compounds. It should be understood that multi-carbide materials may also include other components such as nitrogen, carbide-forming elements that are in elemental form (e.g., that were not converted to a carbide during processing of the multi-carbide material), amongst others including those present as impurities. Typically, but not always, these other components are present in relatively minor amounts (e.g., less than 10 atomic percent).

Suitable carbide forming elements in multi-carbide grinding media of the invention include iron, chromium, hafnium, molybdenum, niobium, rhenium, tantalum, titanium, tungsten, vanadium, zirconium, though other elements may also be suitable. In some cases, the multi-carbide material comprises at least two of these elements. For example, in some embodiments, the multi-carbide material comprises tungsten, rhenium and carbon; in other cases, tungsten, hafnium and carbon; in other cases, molybdenum, titanium and carbon.

Suitable grinding media compositions have been described, for example, in U.S. patent application Ser. No. 11/193,688, filed Jul. 29, 2005, entitled "Grinding Media and Methods Associated With the Same," by Robert Dobbs, which is incorporated herein by reference.

One aspect of the invention is the discovery that using grinding media formed of a material having a certain combination of properties can lead to extraordinary milling performance (e.g., very small milled particle size, very low contamination levels). For example, it has been found that grinding media having the combination of an ultra-high density, a high fracture toughness and a very high hardness can promote such performance.

It may be preferable for the grinding media to be formed of ultra-high density material which is considerably higher than the density of certain conventional grinding media materials. It has been found that ultra-high density grinding media can greatly enhance the efficiency of grinding media in the milling process. For example, in some cases, the grinding media is formed of a material having a density of greater than 8 grams/cubic centimeter; in some cases, the density is greater than 12 grams/cubic centimeter; and, in some cases, the density may even be greater than 15 grams/cubic centimeter (e.g., about 17 grams/cubic centimeter). In some cases, it may be preferable for the density to be less than 30 grams/cubic centimeter. It should be understood that the density of grinding media material may be measured using conventional techniques.

In certain embodiments, it also may be preferable for the grinding media to have a high fracture toughness. It has been found that a high fracture toughness significantly reduces the wearing of grinding media which can lead to unexpectedly low contamination levels in the resulting particle compositions, as described further below. For example, in some cases, the grinding media is formed a material having a fracture toughness of greater than 6 MPa/m1/2; and, in some cases, the fracture toughness is greater than 9 MPa/m1/2. The fracture toughness may be greater than 12 MPa/m1/2 in certain embodiments.

Conventional techniques may be used to measure fracture toughness. Suitable techniques may depend, in part, on the type of material being tested and are known to those of ordinary skill in the art. For example, an indentation fracture toughness test may be suitable in certain cases. Also, a Palmqvist fracture toughness technique may be suitable, for example, when testing hard metals. It should be understood that the fracture toughness values disclosed herein refer to fracture toughness values measured on bulk samples of the material. In some cases, for example, when the grinding media are in the form of very small particles (e.g., less than 150 micron), it may be difficult to measure fracture toughness and the actual fracture toughness may be different than that measured on the bulk samples.

In certain embodiments, it also may be preferable for the grinding media to have a very high hardness. It has been found that media having a very high hardness can lead to increased energy transfer per collision with product material which, in turn, can increase milling efficiency. In some embodiments, the grinding media is formed a material having a hardness of greater than 900 kgf/mm2; and, in some cases, the hardness is greater than 1200 kgf/mm2. The hardness may even be greater than 1700 kgf/mm2 in certain embodiments.

Conventional techniques may be used to measure hardness. Suitable techniques depend, in part, on the type of material being tested and are known to those of ordinary skill in the art. For example, one suitable technique may be Vickers hardness test (following ASTM 1327). It should be understood that the hardness values disclosed herein refer to hardness values measured on bulk samples of the material. In some cases, for example, when the grinding media are in the form of very small particles (e.g., less than 150 micron), it may be difficult to measure hardness and the actual hardness may be greater than that measured on the bulk samples.

A compression test may be used to assess properties (e.g., fracture toughness) of grinding media when in particle form. For example, a "steel plate compression test" may be used. As used herein, a "steel plate compression test" involves placing a single grinding media particle between two polished surfaces of hardened 4140 alloy steel (ASTM A193) and applying a force which compresses the grinding media particle between the surfaces to a point where the grinding media particle fractures or indents at least one of the surfaces. The surfaces can be cut from a rod (e.g., ⅞ inch diameter) and polished using a 0.5 micron diamond polishing disk. A grinding media particle passes the "steel plate compression test" if it does not fracture during the testing and indents at least one of the steel plates. In some cases, methods use grinding media such that at least 70%, or at least 90%, of the grinding media particles are capable of passing the steel plate compression test and have an average particle size of less than about 150 micron (e.g., between 70 micron and 100 micron). In some cases, substantially all of the grinding media particles are capable of passing the steel plate compression test and have an average particle size of less than about 150 micron (e.g., between 70 micron and 100 micron).

It should be understood that grinding media of the invention may have any of the above-described density values combined with any of the above-described fracture toughness values and further combined with any of the above-described hardness values. The particular combination of properties may depend on a number of factors including the ease of forming the grinding media, cost, and desired final particle composition characteristics, amongst others. It should also be understood that, in certain embodiments of the invention, the grinding media may not have a combination of properties that falls within the above-described ranges. In some cases, for example, only certain properties may fall within the above-described ranges.

In some embodiments, the grinding media may have a low wear rate. For example, the grinding media wear rate may be less than 0.01 weight percent/hour milling time. In some cases, the wear rate may be even lower such as less than 0.005%, or less than 0.001% (e.g., about 0.0005%), weight percent/hour milling time.

Grinding media of the invention may have a wide range of dimensions. Regardless of their size, the grinding media may be referred to as particles. In general, the average size of the grinding media is between about 0.5 micron and 10 cm. In certain embodiments, it may be advantageous to use grinding media that are very small. For example, it may be preferred to use grinding media having an average size of less than about 150 microns (e.g., between about 75 and about 125 microns). In some cases, the grinding media may have an average size of less than about 100 microns; or, even less than about 10 microns. In some cases, the grinding media may have an average particle size of greater than 1 micron. The specific dimensions of the grinding media can depend on a variety of factors including starting product material particle size, desired final milled product particle size, as well as grinding media composition, amongst others. In particular, it may be preferred for the size of the grinding media to be between about 10 times and about 100 times larger than the average particle size of the product material prior to milling. It has also been discovered that using very small grinding media (e.g., average size of less than about 150 microns) can lead to surprisingly effective milling performance (e.g., very small particle size, very low contamination levels), particularly when the grinding media also have the above-described properties and/or the compositions (and/or other characteristics) described further below.

It should be understood that the average size of the grinding media may be determined by measuring the average cross-sectional dimension (e.g., diameter for substantially spherical grinding media) of a representative number of grinding media particles.

The grinding media may also have a variety of shapes. In general, the grinding media may have any suitable shape known in the art. In some embodiments, it is preferred that the grinding media are substantially spherical (which is used herein interchangeably with "spherical"). Substantially spherical grinding media have been found to be particularly effective in obtaining desired milling performance.

In some embodiments, the grinding media may be formed of a ceramic material. For example, in some embodiments, it may be preferred for the grinding media to be formed of a multi-carbide material. A multi-carbide material comprises at least two carbide-forming elements (e.g., metal elements) and carbon.

In certain preferred cases, the grinding media are formed of multi-carbide material having the above-noted property combinations. It also may be preferred for the multi-carbide material grinding media to have the very small sizes noted above. Such small sizes have been found particularly effective in certain processes.

A multi-carbide material may comprise a multi-carbide compound (i.e., a carbide compound having a specific stoichiometry; or, a blend of single carbide compounds such as a blend of WC and TiC); or, both a multi-carbide compound and a blend of single carbide compounds. It should be understood that multi-carbide materials may also include other components such as nitrogen, carbide-forming elements that are in elemental form (e.g., that were not converted to a carbide during processing of the multi-carbide material), amongst others including those present as impurities. Typically, but not always, these other components are present in relatively minor amounts (e.g., less than 10 atomic percent).

Suitable carbide-forming elements in multi-carbide grinding media of the invention include iron, chromium, hafnium, molybdenum, niobium, rhenium, tantalum, titanium, tungsten, vanadium, zirconium, though other elements may also be suitable. In some cases, the multi-carbide material comprises at least two of these elements. For example, in some embodiments, the multi-carbide material comprises tungsten, rhenium and carbon; in other cases, tungsten, hafnium and carbon; in other cases, molybdenum, titanium and carbon.

In some embodiments, it may be preferred for the multi-carbide material to comprise at least tungsten, titanium, and carbon. In some of these cases, the multi-carbide material may consist essentially of tungsten, titanium and carbon, and is free of additional elements in amounts that materially affect properties. Though in other cases, the multi-carbide material may include additional metal carbide-forming elements in amounts that materially affect properties.

For example, in these embodiments, tungsten may be present in the multi-carbide material in amounts between 10 and 90 atomic %; and, in some embodiments, in amounts between 30 and 50 atomic %. The amount of titanium in the multi-carbide material may be between 1 and 97 atomic %; and, in some embodiments, between 2 and 50 atomic %. In these embodiments that utilize tungsten-titanium carbide multi-carbide material, the balance may be carbon. For example, carbon may be present in amounts between 10 and 40 atomic %. As noted above, it should also be understood that any other suitable carbide-forming elements can also be present in the multi-carbide material in these embodiments in addition to tungsten, titanium and carbon. In some cases, one or more suitable carbide-forming elements may substitute for titanium at certain sites in the multi-carbide crystal structure. Hafnium, niobium, tantalum and zirconium may be particularly preferred as elements that can substitute for titanium. Carbide-forming elements that substitute for titanium may be present, for example, in amounts of up to 30 atomic % (based on the multi-carbide material). In some cases, suitable multi-carbide elements may substitute for tungsten at certain sites in the multi-carbide crystal structure. Chromium, molybdenum, vanadium, tantalum, and niobium may be particularly preferred as elements that can substitute for tungsten. Carbide-forming elements that substitute for tungsten may be present, for example, in amounts of up to 30 atomic % (based on the multi-carbide material).

It should also be understood that the substituting carbide-forming elements noted above may completely substitute for titanium and/or tungsten to form a multi-carbide material free of tungsten and/or titanium.

It should be understood that other non-multi-carbide grinding media compositions may also be used in certain embodiments of the invention. In particular, non-multi-carbide compositions that have the above-noted combination of properties may be used in certain embodiments. In some cases, these non-multi-carbide compositions may be ceramic materials including ceramics that comprise more than one metal element (but not carbon). Additional, suitable grinding media compositions are described further below.

In general, any suitable process for forming multi-carbide compositions into grinding media having the desired characteristics may be used. Typically, the processes involve heating the components of the multi-carbide material composition to temperatures higher than the respective melting temperatures of the components followed by a cooling step to form the grinding media. A variety of different heating techniques may be used including a thermal plasma torch, melt atomization, and arc melting, amongst others.

A suitable process according to one embodiment of the invention follows. The process involves admixing fine particles of the elements intended to comprise the multi-carbide material in appropriate ratios. The stability of the mixture may be enhanced by introduction of an inert binding agent (e.g., which burns off and does not form a component of the multi-carbide material). The mixture may be subdivided into a plurality of aggregates (e.g., each having a mass approximately equal to that of the desired media particle to be formed). The aggregates may be heated to fuse (e.g., to 90% of theoretical density) and, eventually, melt individual aggregates to form droplets that are cooled to form the grinding media.

The above-described process may be particularly preferred when forming multi-carbide grinding media having relatively small dimensions (e.g., less than 500 micron) and spherical in shape. It should be understood that other dimensions and shapes are also possible by varying process conditions.

As noted above, the grinding media of the present invention are not limited to multi-carbide materials. In certain embodiments of the invention, the grinding media may comprise more than one material component having different compositions. It should be understood that two material components may have a different composition if they comprise different chemical elements or if they comprise the same chemical elements, but present in different amounts (e.g., different stoichiometries). It is also possible for the grinding media to be formed of a single material composition.

The grinding media may be formed of blends of two different materials. For example, the grinding media may be formed of a blend of two different ceramic materials (e.g., a blend of high density ceramic particles in a ceramic matrix); or, a blend of a ceramic material and a metal (e.g., a blend of high density ceramic particles in a metal matrix).

In some multi-component grinding media embodiments, the grinding media comprise coated particles. The particles may have a core material and a coating formed on the core material. The coating typically completely covers the core material, though not in all cases. The composition of the core and coating materials may be selected to provide the grinding media with desired properties and, in some preferred cases, properties within the above-described ranges. One advantage with using a coated structure can be that the core and coating materials may each impart certain selected desired properties (without needing to individually impart all of the desired properties), because the properties of the overall structure are determined by contributions of both the coating and core materials. This can facilitate achieving the desired balance of properties and may allow for more flexibility in grinding media material choice than otherwise would be available in grinding media formed of a single material.

In some embodiments involving coated grinding media, it may be preferable for the core to be formed of a high density material (e.g., greater than 5 grams/cubic centimeter or the other density ranges described above.) The core, for example, may be made of a metal such as steel or depleted uranium; or, a ceramic, such as, tungsten carbide or cemented carbide. In some of these cases, the core material may not have a high fracture toughness and/or hardness.

It may be preferable for the coating material to have a high fracture toughness and/or a high hardness, particularly if the core material does not exhibit such properties but has a high density. The coating, for example, can be formed of a material having the fracture toughness and hardness values described above. Extremely hard materials, such as diamond, can be used as the coating. Also, the coating may be formed of a ceramic material. Suitable ceramic materials include metal carbides (e.g., tungsten carbide), multi-carbides, alumina, zirconium oxide, zirconium silicate, Mg-PSZ, Ce-TZP and Y-TZP. In some cases, to achieve desired properties, the coating can be further toughened by doping with an additive. For example, the coating may be formed of 3Y-TZP that has been further toughened by doping with Sr2Nb2O7.

In some cases, the coating, itself, may have multiple material components. For example, the coating may be formed of more than one layer having different material compositions. In some embodiments, the layers are stacked to form a "superhard" laminate structure. It may be preferable (e.g., to increase hardness) for at least one of the layers in the coating to be relatively thin (e.g., less than 100 nm). In some cases, hardness can be enhanced by having at least one extremely thin layer (or, in some cases, multiple extremely thin layers) having a thickness of less than 10 nm. Particularly when the layers are extremely thin, the laminate structures may include a relatively large number of layers (e.g., greater than 10).

In general, any suitable coating process may be used to produce coated grinding media of the present invention. Such processes include sputtering and evaporative processes.

In certain multi-component grinding media embodiments, the grinding media comprise a composite structure that includes particles dispersed in a matrix material. The composite structure may include, for example, high density (e.g., having any of the ultra-high densities noted above such as 8 grams/cubic centimeter) ceramic particles. The ceramic particles may be dispersed in a ceramic material (e.g., a nitride or a carbide), a metal material, or a blend of ceramic and metal materials. In some embodiments, the ceramic particles may be multi-carbide materials.

In certain cases, the grinding media may be formed of a nanocrystalline composite that includes a plurality of nanoparticles (e.g., particle size of less than 50 nm or even less than 10 nm) dispersed in a matrix material. The matrix may be a ceramic material such as a nitride or carbide. In some cases, it may be preferred for the matrix material to have an amorphous structure (e.g., amorphous silicon nitride, Si3N4). The nanoparticles also may be a ceramic material such as a transition metal nitride (e.g., MenN (Me=Ti, W; V; and the like). The nanoparticles can have a crystalline structure. Such nanocrystalline composites may exhibit an extremely high hardness such as the hardness ranges noted above and, oftentimes, higher. In general, any suitable process may be used to produce nanocrystalline composite grinding media of the present invention.

It should be understood that other grinding media compositions than those described herein may also be used in certain embodiments of the invention. In particular, grinding media compositions that satisfy the desired property ranges described above may be suitable.

Figure 12:
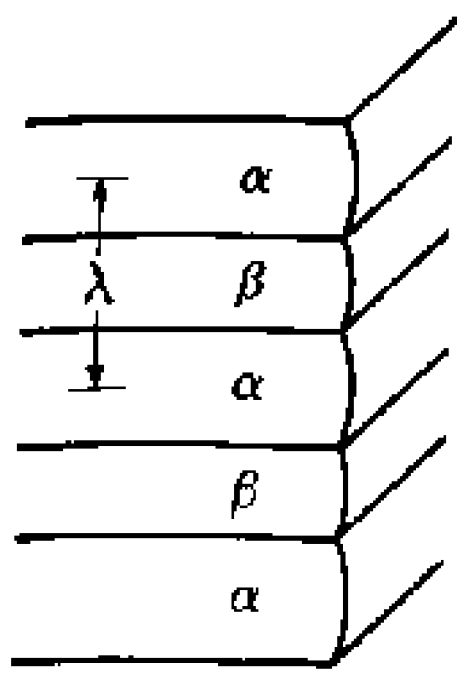
FIG. 12 schematically shows the microstructure of a grinding media particle, according to an embodiment of the invention, which includes $\alpha$ and $\beta$ lamella and an interlamellar spacing ($\lambda$).

The microstructure of grinding media of the invention may also contribute to milling performance in certain cases. It may be preferable for the grinding media to be formed of material have certain interlamellar spacing. Lamella are distinct phases within a material which may be formed upon one another. As shown in FIG. 12, the microstructure of a grinding media includes α and β lamella with the interlamellar spacing (λ) being the distance from the center of one α lamella to the center of the next a lamella.

It has been discovered that using grinding media formed from materials having small interlamellar spacings (e.g., less than 1250 nm) can improve milling performance. In some cases, grinding media formed of material having extremely small interlamellar spacings of less than 100 nm, or even less than 10 nm, may be used to enhance performance. These interlamellar spacings may be achieved, in some cases, by forming a series of very thin film coatings (e.g., less than 100 nm or less than 10 nm) with each film being a different phase. In some cases, the films may comprise materials that are relatively soft (e.g., copper, aluminum), but the overall structure may exhibit a high hardness.

However, it should be understood that grinding media material of the invention may not have the interlamellar spacings that fall within the above ranges; or, that only a portion of the material of an individual grinding media may have such spacing.

The positive effects of the above-noted interlamellar spacings may be found in connection with a wide variety of materials including the compositions noted above. In particular, the milling performance of grinding media formed of ceramic materials such as carbides (including metal carbides (e.g., tungsten, thallium, niobium, and vanadium carbides) or multi-carbides) may significantly benefit from the desirable interlamellar spacings described herein.

In some embodiments, it may be preferred for a majority of the grinding media used in a milling process to have substantially the same composition and/or properties. That is, at least greater than 50% of the grinding media used in the process has substantially the same composition and/or properties. In some embodiments, greater than 75%, greater than 90%, or substantially all of the grinding media may have substantially the same composition and/or properties As noted above, grinding media of the present invention can be used in milling processes. The grinding media are suitable for use in a wide range of conventional mills having a variety of different designs and capacities. Suitable types of mills include, but are not limited to, ball mills, rod mills, attritor mills, stirred media mills, and pebble mills, amongst others.

In some cases, conventional milling conditions (e.g., energy, time) may be used when processing with grinding media of the invention. In other cases, grinding media of the invention may enable use of milling conditions that are significantly less burdensome (e.g., less energy, less time) than those of typical conventional milling processes, while achieving equivalent or superior milling performance, as described further below. In some cases, grinding media having the above-described combinations of hardness, toughness, and density properties allow processing under conditions that would be detrimental to conventional grinding and milling media.

A typical milling process involves introduction of a slurry of product material (i.e., feed material) and a milling fluid (e.g., water or methanol) into a processing space in a mill in which the grinding media are confined. The viscosity of the slurry may be controlled, for example, by adding additives to the slurry such as dispersants. The mill is rotated at a desired speed and product material particles are admixed with the grinding media. The collisions between product material particles and grinding media result in reducing the size of the product material particles. In certain processes, it is believed that the mechanism for particle size reduction is dominated by wearing of product material particle surfaces; while, in other processes, it is believed the mechanism for particle size reduction is dominated by particle fracture. The particular mechanism may effect the final characteristics (e.g., morphology) of the milled particle composition. The product material is typically exposed to the grinding media for a certain mill time after which the milled product material is separated from the grinding media using conventional techniques, such as washing and filtering, or gravity separation. In some processes, the product material slurry is introduced through a mill inlet and, after milling, recovered from a mill outlet. The process may be repeated and, in certain processes, a number of mills may be used sequentially with the outlet of one mill being fluidly connected to the inlet of the subsequent mill.

Grinding media of the invention, in particular those having the above-noted properties and/or compositions, have been found to provide extraordinary milling performance (e.g., very small milled particle size, very low contamination levels). Certain milling processes of the invention can produce milled particle compositions having an average particle size of less than 500 nm. It is possible to produce considerably smaller particles using grinding media of the invention. For example, the grinding media can produce milled particle compositions having an average particle size of less than 100 nm; less than 50 nm; or, even less than 10 nm. In some processes, these particle sizes are achieved when the feed material (prior to milling) has an average particle size of greater than 1 micron, greater than 10 micron, or even greater than 50 micron. In some processes, the average particle size of the feed material may be greater than 10 times, 50 times, 100 times, or even greater than 500 times the average particle size of the milled material. The specific particle size of the milled material depends on a number of factors including milling conditions (e.g., energy, time), though is also dictated, in part, by the application in which the milled material is to be used. In general, the milling conditions may be controlled to provide a desired particle size. In some cases, though not all, it may be preferable for the particle size to be greater than 1 nm to facilitate processing. The particle size of the feed material may depend on commercial availability, amongst other factors.

An important (and surprising) advantage of certain grinding methods of the invention is that the above-noted particle sizes can be achieved at very low contamination levels. The grinding media properties and/or compositions noted above may enable the low contamination levels because such characteristics lead to very low wear rates. For example, the contamination levels may be less than 900 ppm, less than 500 ppm, less than 200 ppm, or even less than 100 ppm. In some processes, virtually no contamination may be detected which is generally representative of contamination levels of less than 10 ppm. As used herein, a "contaminant" is grinding media material introduced into the product material composition during milling. It should be understood that typical commercially available product materials may include a certain impurity concentration (prior to milling) and that such impurities are not includes in the definition of contaminant as used herein. Also, other sources of impurities introduced in to the product material, such as material from the milling equipment, are not included in the definition of contaminant as used herein. The "contamination level" refers to the weight concentration of the contaminant relative to the weight concentration of the milled material. Typical units for the contamination level are ppm. Standard techniques for measuring contamination levels are known to those of skill in the art including chemical composition analysis techniques.

It should be understood that methods of the invention may produce compositions having any of the above-described particle size values (including values of relative size between particles before and after milling) combined with any of the above-described contamination levels. For example, one method of the invention involves milling feed particles having an average initial particle size to form a milled particle composition having an average final particle size of less than 100 nm, wherein the initial particle size is greater than 100 times the final particle size and the milled particle composition has a contamination level of less than 500 ppm It should also be understood that, in certain embodiments of the invention, the grinding processes may not produce milled particle compositions having the above-described particles sizes and/or contamination levels. In some cases, for example, only some of these characteristics may fall within the above-described ranges. Also, grinding media of the invention can be used to produce milled particle compositions having much larger particle sizes than those described above, in particular when the particle size of the product material before milling is very large (e.g., on the order of centimeters or greater).

It should be understood that milled particles have a characteristic "milled" morphology. Those of ordinary skill in the art can identify "milled particles" as particles that include one or more of the following microscopic features: multiple sharp edges, faceted surfaces, and being free of smooth rounded "corners" such as those typically observed in chemically-precipitated particles.

It should be understood that "substantially spherical" milled particles, as described herein, may still have one or more of the above-described microscopic features, while appearing substantially spherical at lower magnifications. In certain embodiments, it may be preferred for milled particles of the invention to be substantially spherical. In other cases, the milled particles may have platelet, oblate spheroid, and/or lens shapes. Other particle shapes are also possible. It should be understood that within a milled particle composition, individual particles may be in the form of one or more of the above-described shapes.

Advantageously, the grinding media enable advantageous milling conditions. For example, lower milling times and specific energy inputs can be utilized because of the high milling efficiency of the grinding media of the invention. As used herein, the "specific energy input" is the milling energy consumed per weight product material. Even milled particle compositions having the above-noted particle sizes and contamination levels can be produced at low milling input energies and/or low milling times. For example, the specific energy input may be less than 125,000 kJ/kg; or less than 90,000 kJ/kg. In some cases, the specific energy input may be even lower such as less than 50,000 kJ/kg or less than 25,000 kJ/kg. The actual specific energy input and milling time depends strongly on the composition of the product material and the desired reduction in particle size, amongst other factors. For example, grinding media of the invention may be used to produce a titania milled particle composition at a specific energy input of less than about 25,000 kJ/kg (e.g., about 20,000 kJ/kg), an average particle size of less than about 100 nm (e.g., about 80 nm) and a contamination level of less than 500 ppm, wherein the titania feed particles have an average particle size (e.g., about 600 nm) of greater than 50 times the average particle size of the milled titania particle composition.

It should be understood that the grinding media can be used to process a wide variety of product materials including organic and inorganic materials. In general, the grinding processes of the invention are not limited to any specific material types. Though, it is notable that the grinding media can be used to produce the very small milled particle size and very low contamination levels noted above even when using inorganic product materials such as ceramics. Suitable product materials include metals (such as cobalt, molybdenum, titanium, tungsten), metal compounds (such as intermetallic compounds, metal hydrides or metal nitrides), metal alloys, ceramics (including oxides, such as titanium oxide (titania), aluminum oxide (Al2O3), and carbides such as silicon carbide) and diamond, amongst many others. Certain materials are described in connection with specific methods of the invention further below.

In some embodiments, it may be preferred for the multi-carbide material to comprise at least tungsten, titanium and carbon. In some of these cases, the multi-carbide material may consist essentially of tungsten, titanium and carbon, and is free of additional elements in amounts that materially affect properties. Though in other cases, the multi-carbide material may include additional metal carbide forming elements in amounts that materially affect properties. For example, in these embodiments, tungsten may be present in the multi-carbide material in amounts between 10 and 90 atomic %; and, in some embodiments, in amounts between 30 and 50 atomic %. The amount of titanium in the multi-carbide material may be between 1 and 97 atomic %; and, in some embodiments, between 2 and 50 atomic %. In these embodiments that utilize tungsten-titanium carbide multi-carbide material, the balance may be carbon. For example, carbon may be present in amounts between 10 and 40 atomic %. As noted above, it should also be understood that any other suitable carbide forming elements can also be present in the multi-carbide material in these embodiments in addition to tungsten, titanium and carbon. In some cases, one or more suitable carbide forming elements may substitute for titanium at certain sites in the multi-carbide crystal structure. Hafnium, niobium, tantalum and zirconium may be particularly preferred as elements that can substitute for titanium. Carbide forming elements that substitute for titanium may be present, for example, in amounts of up to 30 atomic % (based on the multi-carbide material). In some cases, suitable multi-carbide elements may substitute for tungsten at certain sites in the multi-carbide crystal structure. Chromium, molybdenum, vanadium, tantalum, and niobium may be particularly preferred as elements that can substitute for tungsten. Carbide forming elements that substitute for tungsten may be present, for example, in amounts of up to 30 atomic % (based on the multi-carbide material).

It should also be understood that the substituting carbide forming elements noted above may completely substitute for titanium and/or tungsten to form a multi-carbide material free of tungsten and/or titanium.

It should be understood that grinding media compositions that are not disclosed herein but have certain above-noted characteristics (e.g., high density) may be used in embodiments of the invention. Milling processes of the present invention are not limited to the grinding media compositions described herein.

In general, any suitable process for forming grinding media compositions having the desired characteristics may be used. In some cases, the processes involve heating the components of the composition to temperatures higher than the respective melting temperatures of the components followed by a cooling step to form the grinding media. A variety of different heating techniques may be used including a thermal plasma torch, melt atomization, and arc melting, amongst others. For example, one suitable process involves admixing fine particles of the elements intended to comprise the grinding media in appropriate ratios. The stability of the mixture may be enhanced by introduction of an inert binding agent (e.g., which burns off and does not form a component of the grinding material). The mixture may be subdivided into a plurality of aggregates (e.g., each having a mass approximately equal to that of the desired media particle to be formed). The aggregates may be heated to fuse (e.g., to 90% of theoretical density) and, eventually, melt individual aggregates to form droplets that are cooled to form the grinding media.

In some embodiments, the grinding media may be formed of two different materials. For example, the grinding media may be formed of a blend of two different ceramic materials (e.g., a blend of high density ceramic particles in a ceramic matrix); or a blend of a ceramic material and a metal (e.g., a blend of high density ceramic materials in a metal matrix).

In some embodiments in which the grinding media comprises more than one material component, the grinding media may comprise coated particles. The particles may have a core material and a coating formed on the core material. The coating typically completely covers the core material, but not in all cases. The composition of the core and coating materials may be selected to provide the grinding media with desired properties such as a high density. For example, the core material may be formed of a high density material (e.g., greater than 8 grams/cm$^3$). The core, for example, may be formed of a metal such as steel or depleted uranium; or a ceramic such as a metal carbide.

As noted above, particle compositions may be produced in a milling process that use grinding media as described herein. The processes may utilize a wide range of conventional mills having a variety of different designs and capacities. Suitable types of mills include, but are not limited to, ball mills, rod mills, attritor mills, stirred media mills, pebble mills and vibratory mills, among others.

In some cases, conventional milling conditions (e.g., energy, time) may be used to process the particle compositions using the grinding media described herein. In other cases, the grinding media described herein may enable use of milling conditions that are significantly less burdensome (e.g., less energy, less time) than those of typical conventional milling processes, while achieving a superior milling performance (e.g., very small average particle sizes).

One aspect of the invention is that small particle compositions may be produced using very low specific energy input (i.e., energy consumed in milling process per weight of feed material). The preferred grinding media described above may enable advantageous milling conditions. For example, lower milling times and specific energy inputs can be utilized because of the high milling efficiency of the grinding media. As used herein, the "specific energy input" is the milling energy consumed per weight product material. Even milled particle compositions having the above-noted particle sizes and contamination levels can be produced at low milling input energies and/or low milling times. For example, the specific energy input may be less than 125,000 kJ/kg; or less than 90,000 kJ/kg. In some cases, the specific energy input may be even lower such as less than 50,000 kJ/kg or less than 25,000 kJ/kg. The actual specific energy input and milling time depends strongly on the composition of the product material and the desired reduction in particle size, amongst other factors. For example, grinding media of the invention may be used to produce a titania milled particle composition at a specific energy input of less than about 25,000 kJ/kg (e.g., about 20,000 kJ/kg), an average particle size of less than about 100 nm (e.g., about 80 nm) and a contamination level of less than 500 ppm, wherein the titania feed particles have an average particle size (e.g., about 600 nm) of greater than 50 times the average particle size of the milled titania particle composition.

Milling processes of the invention typically involve the introduction of a slurry of feed material and a milling fluid (e.g., water or non-aqueous fluids) into a processing space in a mill in which the grinding media are confined. The viscosity of the slurry may be controlled, for example, by adding additives to the slurry such as dispersants. The mill is rotated at a desired speed and material particles mix with the grinding media. Collisions between the particles and the grinding media can reduce the size of the particles. In certain processes, it is believed that the mechanism for particle size reduction is dominated by wearing of particle surfaces; while, in other processes, it is believed the mechanism for particle size reduction is dominated by particle fracture. The particular mechanism may affect the final particle characteristics (e.g., morphology, topography). The particles are typically exposed to the grinding media for a certain mill time after which the milled material is separated from the grinding media using conventional techniques, such as washing and filtering, screening or gravitation separation.

It should be understood that, in certain methods, the goal of the milling process may be to produce surface features (e.g., morphology, topography, crystallographic orientation) on the particles rather than to reduce particle size. In these methods, particle size also may be reduced, though the particle size reduction may be negligible in some cases. For example, these methods may involve recovering milled nanoparticles having one or more desired surface features and an average particle size within about 25%, or within about 10%, of the average particle size of the feed particles. In some embodiments, the milled nanoparticles may even have substantially the same average particle size as the feed particles.

To produce desired surface features on the nanoparticles, milling conditions are appropriately selected. For example, the specific energy input may be selected to be relatively low when providing surface features without significantly reducing particle size. It should be understood that the specific milling conditions strongly depend on the particle material composition.

In some embodiments, the milling process may be used to form a region (or regions) of a second material composition on surfaces of particles having a first material composition. In these cases, particles having the first and the second composition are milled simultaneously. The milling process may fracture portions of particles of the second composition and such portions may be deposited on surfaces of particles of the first composition.

The particle compositions of the invention may be used in a wide variety of applications. In general, any application that uses small particles may be suitable. As noted above, catalytic applications (such as in fuel cells) may be particularly preferred.

The following examples are not intended to be limiting in any way.

Example 1

This example compares the catalytic activity of a particle composition produced according to an embodiment of the invention to a commercially-available particle composition.

A titania (rutile) particle composition having an average particle size of less than 150 nm was prepared using a milling process of the present invention. A commercially available titania (rutile) particle composition was obtained. A chemisorption technique was used to assess catalytic activity of the two compositions by evaluating quantitatively the number of surface active sites which are likely to promote (catalyze) chemical reactions. The chemisorption technique used ammonia isotherms that give a quantitative measure of the chemisorbed and physisorbed ammonia on the samples. The milled titania composition of the invention showed an increase in ammonia uptake of greater than 50% than the commercially available titania composition.

This result shows that the milled titania composition of the invention is significantly more catalytically active than the commercially available titania composition.

Example 2

This example compares the catalytic activity of fuel cell catalyst particle compositions produced according to an embodiment of the invention to a fuel cell catalyst particle composition produced according to a conventional process.

PtBi particle compositions having an average particle size of 15 nm (A1), an average particle of 30 nm (A2), and an average particle size of 10 nm (A3) were prepared using a milling process of the present invention. PtBi particle compositions having an average particle size of 19 nm (C1), 4-5 nm (C2) and 4-5 nm (C3) produced using a conventional chemical precipitation process were obtained.

Following reductive pre-treatment cleaning, cyclic voltammetry (CV) was performed on each particle composition. A potential range of −0.2V to 0.2V at 10 mV/s sweep rate was probed. Typically three cycles were executed.

All electrochemical evaluations were performed in a standard 3-electrode electrochemical cell. The volume of solution in the cell was approx. 50 mL. Deoxygenated 10M formic acid with no supporting electrolyte was used in the electrochemical evaluations. A counter electrode of Pt wire was used. A reference electrode of Ag/AgCl (sat'd NaCl) was used. Experiments were conducted at room temperature. All electrochemical data and procedures were recorded using a Potentiostat/Galvanostat Model 283 (EG&G Instruments, Princeton Applied Research) controlled with the CorrWare 2 software package (Solartron Analytical).

Figure 2:
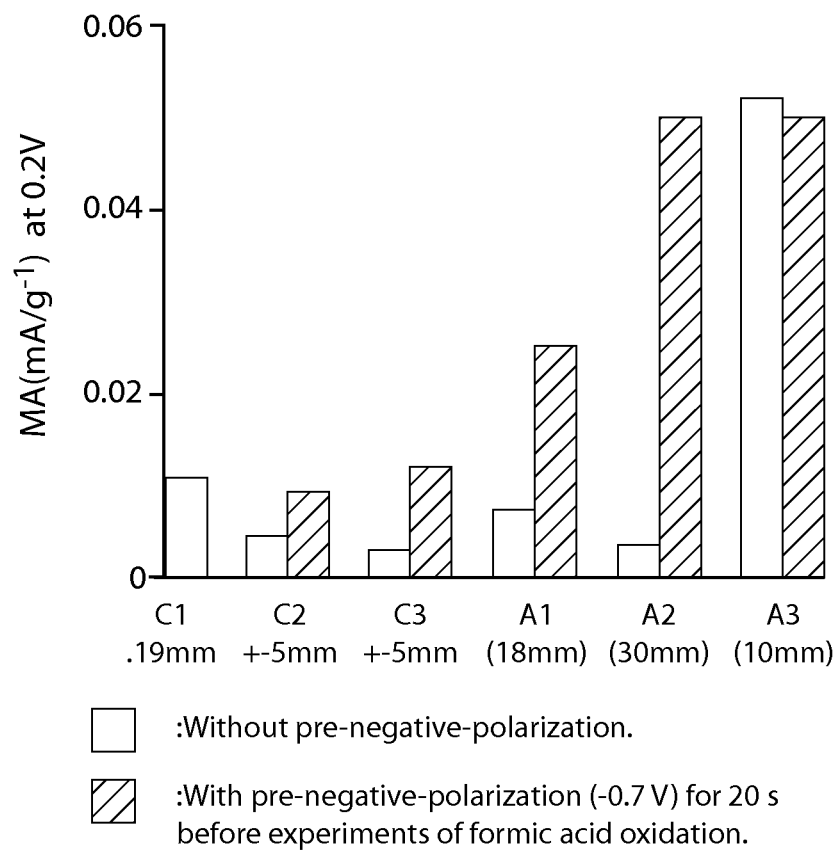
FIG. 2 shows the results of the cyclic voltammetry (CV) measurements made in Example 2.

FIG. 2 shows the current obtained for each sample. The results show that fuel cell catalyst particle compositions produced according to an embodiment of the invention exhibit significantly higher catalytic behavior compared to the fuel cell catalyst particle composition produced according to the conventional process.

Example 3

This example illustrates characterization of an alumina particle composition produced according to an embodiment of the invention.

Figure 3A:
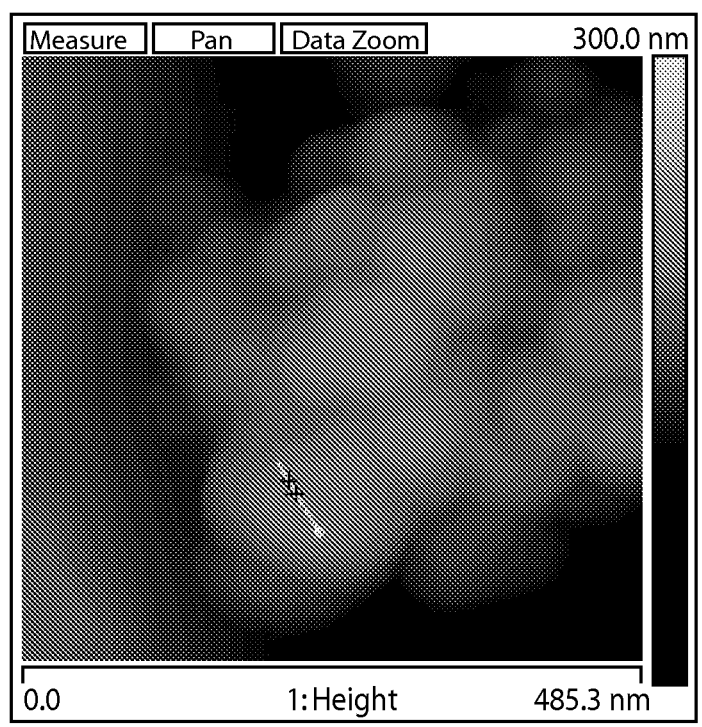
FIG. 3A is a copy of an AFM image of a representative region of the particle composition described in Example 3.
Figure 3B:
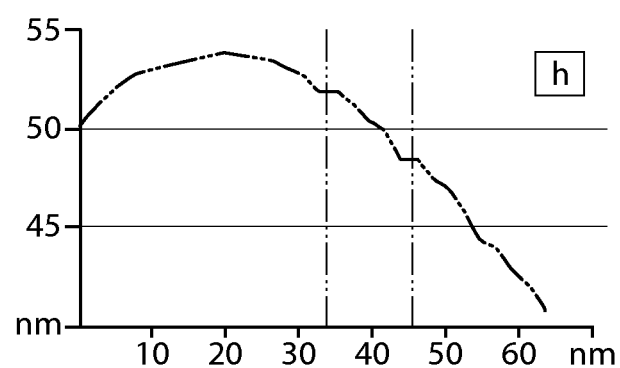
FIG. 3B is a height vs. distance plot of the line on the image in FIG. 3A.

An alumina particle composition having an average particle size of less than 150 nm was prepared using a milling process of the present invention. Atomic Force Microscopy (AFM) was used to characterize the particles. The analysis showed that the particles had a lenticular morphology. The particles generally had a thickness of about 10 nm and a length of about 60 nm in length. FIG. 3A is a copy of an AFM image of a representative region of the particle composition. FIG. 3B is a height vs. distance plot of the line on the image in FIG. 3A. FIG. 3B shows a few atomic steps having a height of about 6 nm with the remaining steps being below the resolution of the AFM.

Figure 4:
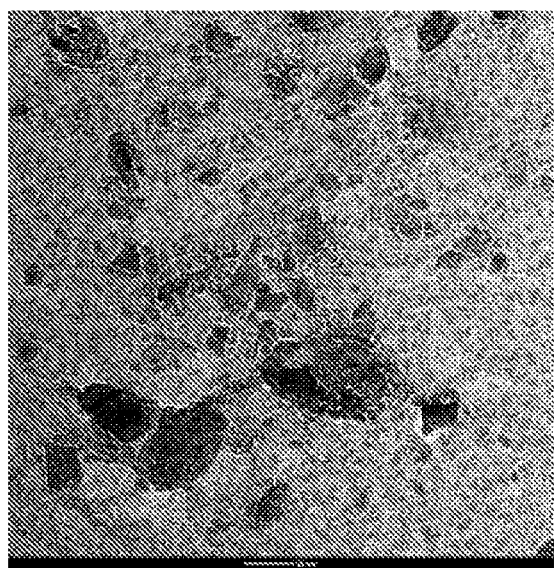
FIG. 4 is a copy of a TEM image of the alumina particles described in Example 3.
Figure 5:
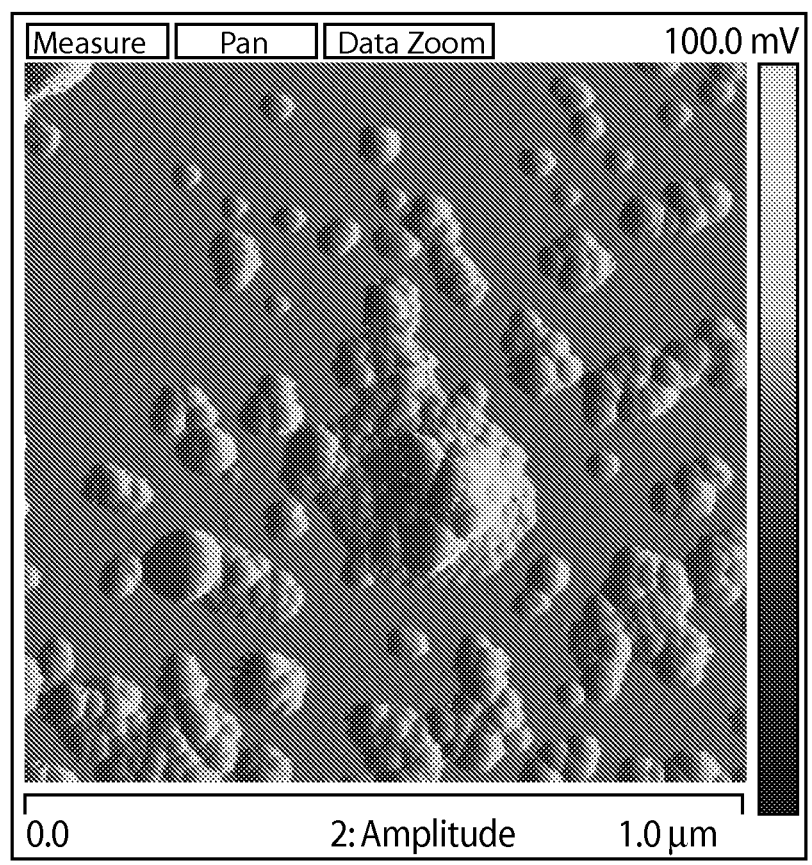
FIGS. 5-7, 8A, 9A and 10 are copies of AFM images of the silicon particles described in Example 4.
Figure 6:
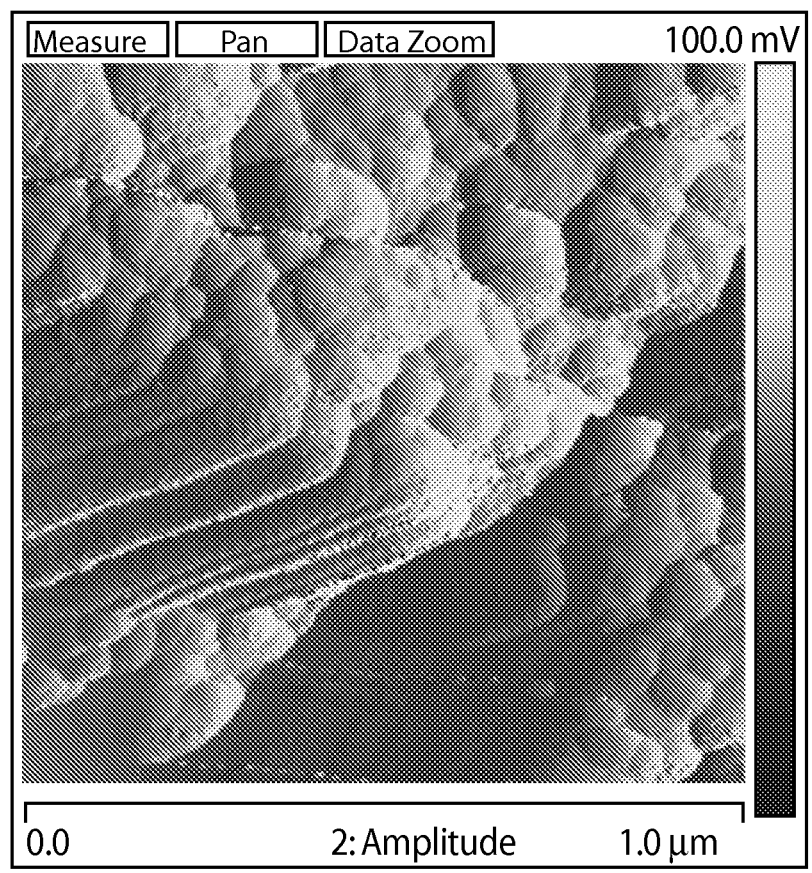
Figure 7:
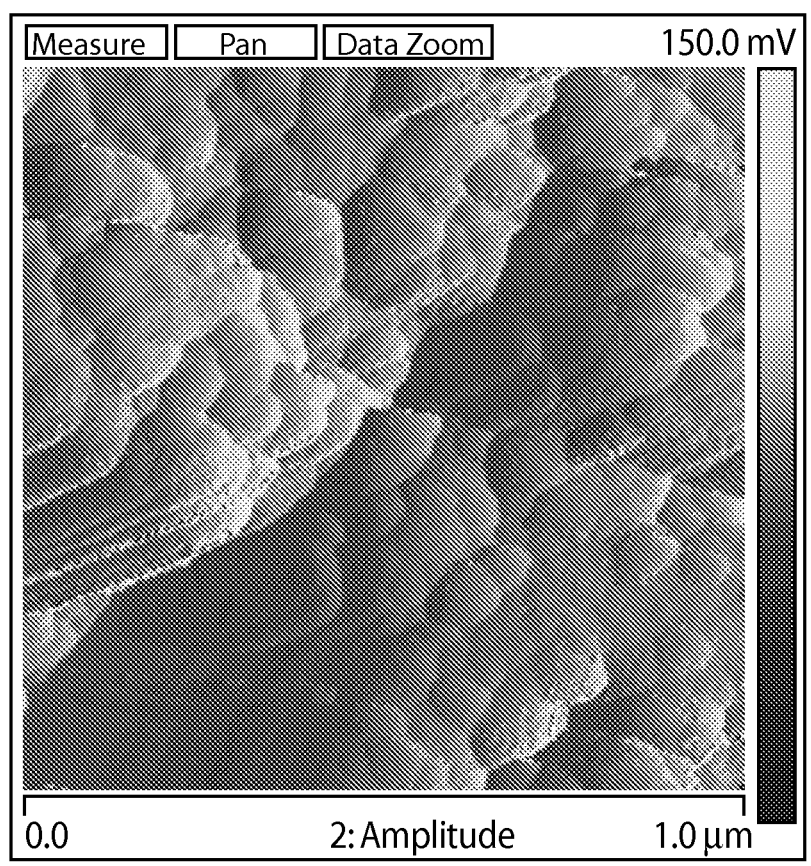

FIG. 4 is a TEM image performed on these nanoparticles and TEM confirmed a platelet (e.g., lenticular) structure with a preferred orientation. XRD was also performed showing alpha alumina phase.

Example 4

This example illustrates characterization of a silicon particle composition produced according to an embodiment of the invention.

Figure 8A:
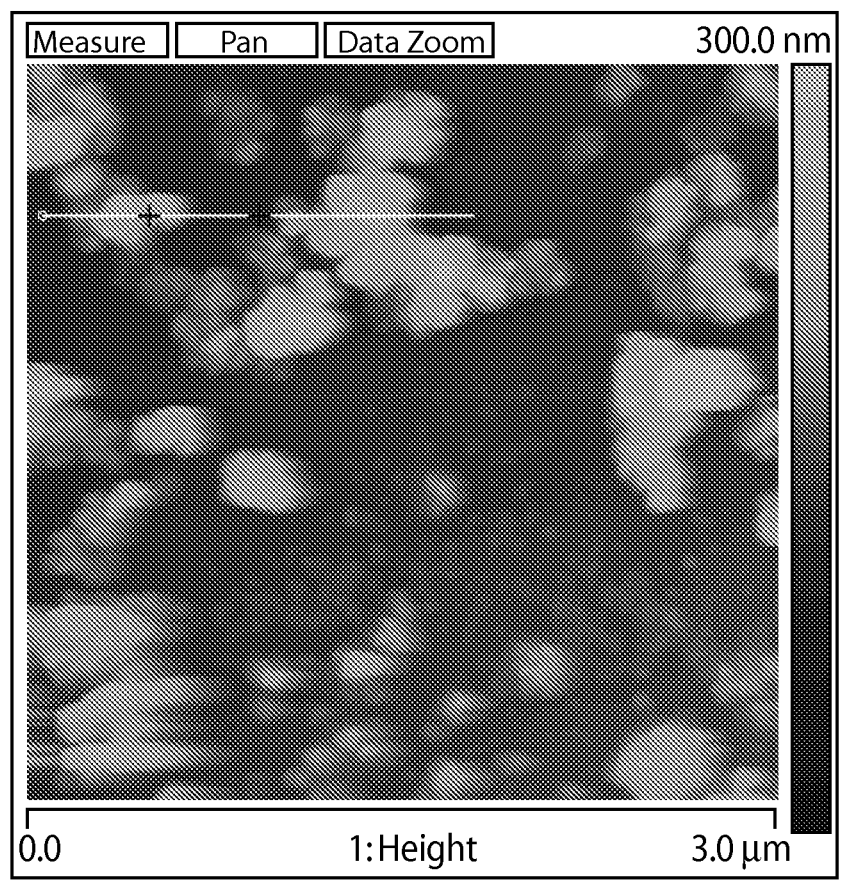
Figure 8B:
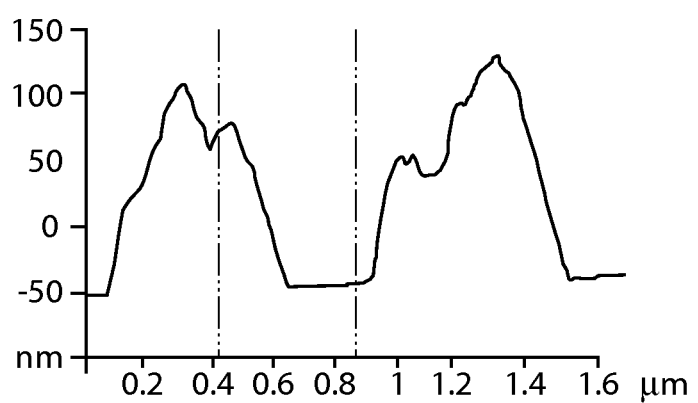
FIGS. 8B and 9B are respective height vs. distance plots of the lines on FIGS. 8A and 9A.
Figure 9A:
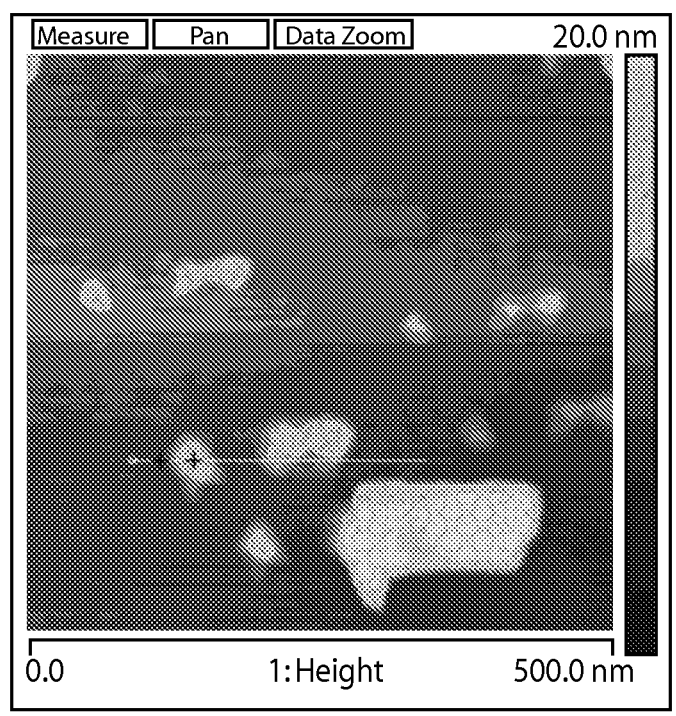
Figure 9B:
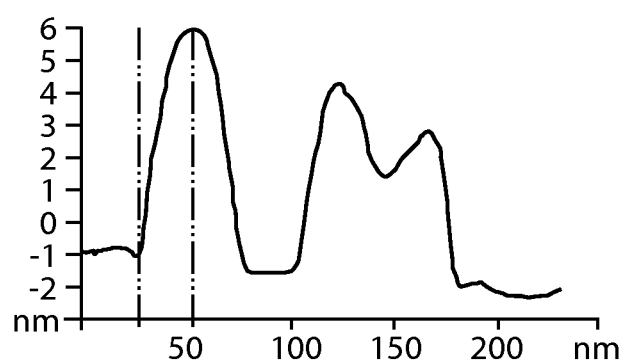
Figure 10:
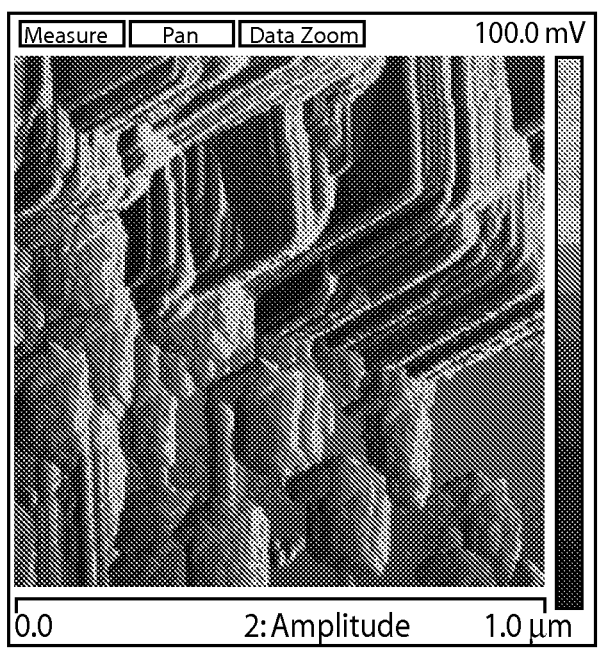
Figure 11:
FIG. 11 is a copy of an FETEM image of the silicon particles described in Example 4.

A silicon particle composition having an average particle size of less than 150 nm was prepared using a milling process of the present invention. The particle composition was characterized using a number of techniques including AFM. Copies of AFM images of the composition are shown in FIGS. 5-10. FIGS. 8B and 9B are height vs. distance plots of the lines on FIGS. 8A and 9A, respectively. The particles were about 50 nm in length and 6 nm in thickness.

The particle size calculated by using BET equivalent spherical diameter indicates that the particle size was smaller than the size measured by using an acoustic instrument (e.g., DT-1200 acoustic spectrometer) and TEM. This is an additional indication that the particles were not spherical, but platelet. Additionally, the AFM images show the particles appeared to be substantially flat. A majority of the particles appear to have been fractured on the (111) planes to produce "flakes" that may be later reduced to small flat particles as the milling process proceeds. The milling process produced nanoscale, flat particles even on a silicon material including a cubic crystal structure.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for milling product in a mill using grinding media comprising:
   providing grinding media particles formed of a ceramic material, the ceramic material having an interlamellar spacing of less than 1250 nm; and
   milling product in a mill using the grinding media.

2. The method of claim 1, wherein the interlamellar spacing is less than 100 nm.

3. The method of claim 1, wherein the interlamellar spacing is less than 10 nm.

4. The method of claim 1, wherein the grinding media particles have an average size of less than about 150 micron.

5. The method of claim 1, wherein the grinding media have a size of less than 500 micron.

6. The method of claim 1, comprising milling the product to a size of less than 100 nanometers.

* * * * *